United States Patent [19]

Okuyama et al.

[11] Patent Number: 5,391,486
[45] Date of Patent: Feb. 21, 1995

[54] PHYSIOLOGICALLY ACTIVE SUBSTANCE BE-16627

[75] Inventors: Akira Okuyama; Nobuo Kanbayashi; Kyozo Naito; Hajime Suzuki; Shigeru Nakajima; Hiroyuki Suda, all of Tokyo; Masanori Okanishi, Kawasaki, all of Japan

[73] Assignee: Banyu Pharmaceutical Co., Ltd., Tokyo, Japan

[21] Appl. No.: 720,828

[22] Filed: Jul. 11, 1991

[30] Foreign Application Priority Data

Nov. 24, 1989 [JP] Japan .................. 1-305764

[51] Int. Cl.$^6$ .............. C07C 229/08; C12N 1/20; C12P 21/02
[52] U.S. Cl. .............. 435/71.2; 435/253.5; 514/19; 562/561; 562/564
[58] Field of Search .............. 514/19; 435/71.2, 253.5; 562/561, 564

[56] References Cited

U.S. PATENT DOCUMENTS

| | | | |
|---|---|---|---|
| 4,259,450 | 3/1981 | Argoudelis et al. | 435/253.5 |
| 4,288,556 | 9/1981 | Belloc et al. | 435/253.5 |
| 4,496,540 | 1/1985 | Kim | 514/19 |
| 4,880,735 | 11/1989 | Fayerman et al. | 435/71 |
| 4,996,358 | 2/1991 | Handa et al. | 562/621 |

FOREIGN PATENT DOCUMENTS

0231081A2  8/1987  European Pat. Off. .
0236872A3  9/1987  European Pat. Off. .

OTHER PUBLICATIONS

Dispasquale, Gene et al., "Proteoglycan- and Collagen-Degrading Enzymes from Human Interleukin 1-Stimulated Chondrocytes from Several Species: Proteoglycanase and Collagenase Inhibitors as Potentially New Disease-Modifying Antiarthritic Agents," *Proceedings of the Society for Experimental Biology and Medicine* 183:262–276, 1987.

Wilhelm, Scott M. et al., "Human skin fibroblast stromelysin: Structure, glycosylation, substrate specificity, and differential expression in normal and tumorigenic cells," *Proc. Natl. Acad. Sci. USA* 84:6725–6729, 1987.

"Metalloproteinase inhibitor-producing Streptomyces strains," *Chemical Abstracts* 96:197874z, 1982.

*Primary Examiner*—Jeffrey E. Russel
*Attorney, Agent, or Firm*—Seed and Berry

[57] ABSTRACT

The present invention relates to new stromelysin (human)-inhibitors, i.e., physiologically active substances BE-16627 represented by the general formula:

$$\begin{array}{c}
R\phantom{xxx}CH_3\\
\phantom{xxxx}\diagdown\phantom{x}\diagup\\
\phantom{xxxxx}CH\phantom{xxxxx}OH\\
\phantom{xxxxx}|\phantom{xxxxxxx}|\\
\phantom{xxxxx}CH_2\phantom{xxxx}CH_2\\
HO-NH-CO-CH_2-CH-CO-NH-CH-CO-\\
\phantom{xxxxxxxxxxxxxxxxxx}H_3C\phantom{xx}CH_3\\
\phantom{xxxxxxxxxxxxxxxxxxxxx}\diagdown\phantom{x}\diagup\\
\phantom{xxxxxxxxxxxxxxxxxxxxxx}CH\\
\phantom{xxxxxxxxxxxxxxxxxxxxxx}|\\
\phantom{xxxxxxxxxxxxxxx}-NH-CH-COOH
\end{array} \quad [\text{I}]$$

wherein R represents a hydrogen atom or a methyl group, or pharmaceutically acceptable salts thereof, a process for the production and use thereof, and a microorganism producing the substance BE-16627.

2 Claims, 8 Drawing Sheets

PHYSIOLOGICALLY ACTIVE SUBSTANCE BE-16627

TECHNICAL FIELD

The present invention relates to novel inhibitors for stromelysin (human), which inhibitors are useful in the field of pharmaceuticals, and more particularly, can be used for a treatment and prophylaxis of metastasis and infiltration of cancer cells, rheumatoid arthritis, gingival inflammation, and glomerulonephritis, caused by degradation of outercellular matrix by proteases, a process for the production and use thereof, and a microorganism producing the inhibitor substances.

BACKGROUND ART

It is known that stromelysin (human) has a wide substrate specificity spectrum, degrades many kinds of proteins including cancer cell matrix (IV-and IX-type collagens, laminin, proteroglycan, fibronectin, casein, elastin and gelatin) (J. Biol. Chem. Vol. 261, pp 14245–14255, 1986), and causes diseases such as rheumatoid arthritis (literature referred to above), metastasis of cancer cells (Proc. Natl. Acad. Sci., USA Vol. 83, pp 9413–9417, 1986), gingival inflammation (J. Periodont, et al. Res. Vol. 17, pp 183–190, 1982), glomerulonephritis (The Kidney, third ed. Vol. 1, pp 939–945, edited by Glassock, R. J., W. B. Sanders Co. Philadelphia), and the like, caused by a destruction of the outercellular matrix. Moreover, collagen has an important role in the destruction of the outercellular matrix (Arthritis Rheum., Vol. 27, pp 285–290, 1980), and stromelysin activates a precursor of collagenase (procollagenase), and indirectly, takes part in a control of collagenase activity (Biochem. J. Vol. 248, pp 265–268, 1987). Accordingly, to provide an inhibitor specific to stromelysin or collagenase is useful for treatment and prophylaxis of diseases in which these enzymes are involved, but to date, such an inhibitor having a low toxicity has not been developed.

Under the above circumstances, there is need for the development of a low molecular weight and low toxic inhibitor for stromelysin (human).

The present inventors, as a result of screening a wide range of microbial metabolites for a substance having an inhibitory activity to stromelysin (human), found that compounds represented by the general formula described hereinafter exhibit a remarkable stromelysin-inhibitory activity, and thus accomplished the present invention.

DISCLOSURE OF THE INVENTION

The present invention relates to a physiologically active BE-16627 substances represented by the general formula:

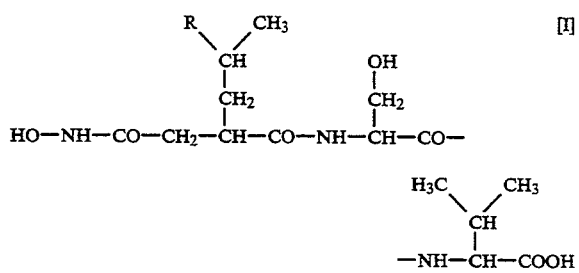

wherein R represents a hydrogen atom or a methyl group, or pharmaceutically acceptable salts thereof, a process for the production and use thereof, and a microorganism producing the BE-16627 substances.

Herein, the compound wherein R is a hydrogen atom is designated BE-16627A, and the compound wherein R is a methyl group is designated BE-16627B.

Next, the physico-chemical properties of the present compounds are shown.

Physico-chemical properties of BE-16627A
Appearance: colorless amorphous solid or crystal
Molecular formula: $C_{15}H_{27}N_3O_7$
Elementary analysis: Theoretical: C 49.85%, H 7.53%, N 11.63% Found : C 49.81%, H 7.52%, N 11.68%
Mass spectrum: FAB Mass spectrum as shown in FIG. 1. (362. 1941, [M+H]+)
UV spectrum: end absorption (solvent: methanol)
IR spectrum: IR spectrum obtained by KBr tablet method as shown in FIG. 2.
$^1$H-NMR spectrum: $^1$H-NMR spectrum (300 MHz) measured in $d_6$-dimethylsulfoxide as shown in FIG. 3.
$^{13}$C-NMR spectrum: $^{13}$C-NMR spectrum (75 MHz) measured in $d_6$-dimethylsulfoxide as shown in FIG. 4.
Melting point: 90°–100° C.
Optical rotation $[\alpha]_D^{20}$: −20.1 (C=0.417, methanol)
Solubility: readily soluble in an alkaline water, but almost insoluble in an organic solvent such as chloroform, ethyl acetate, benzene, hexane and the like.
Clasification for acidic, neutral or basic substance: acidic substance.
Rf value: 0.65 (on Kiesel gel 60, Merck; developing solvent: n-butanol/acetic acid/water=4:1:2)
Color reaction: Rydon Smith reaction: positive Ferric chloride reaction: positive Physico-chemical properties of BE-16627B
Appearance: Colorless amorphous solid or crystal
Molecular formula: $C_{16}H_{29}N_3O_7$
Elementary analysis: Theoretical: C 51.19%, H 7.79%, N 11.19% Found: C 51.17%, H 7.70%, N 11.23%
Mass spectrum: FAB Mass spectrum as shown in FIG. 5. (376. 2055, [M+H]+)
UV spectrum: end absorption (solvent: methanol)
IR spectrum: IR spectrum obtained by KBr tablet method as shown in FIG. 6.
$^1$H-NMR spectrum: $^1$H-NMR spectrum (300 MHz) measured in $d_6$-dimethylsulfoxide as shown in FIG. 7.
$^{13}$C-NMR spectrum: $^{13}$C-NMR spectrum (75 MHz) measured in $d_6$-dimethylsulfoxide as shown in FIG. 8.
Melting point: 95°–105° C.
Optical rotation $[\alpha]_D^{20}$: −9.1 (C=0.417, methanol)
Solubility: readily soluble in an alkaline water, but almost insoluble in an organic solvent such as chloroform, ethyl acetate, benzene, hexane and the like.
Classification for acidic, neutral or basic substance: acidic substance.
Rf value: 0.69 (on Kiesel gel 60, Merck; developing solvent: n-butanol/acetic acid/water=4:1:2)
Color reaction: Rydon Smith reaction: positive Ferric chloride reaction: positive Biological activities of the present BE-16627A and B An inhibitory activity of BE-16627A and B to various proteases including stromelysin and collagenase was determined by an in-vitro test. As stromelysin (human), prostromelysin prepared by genetic engineering (Celltech., GB) was used by treating it with trypsin (10 μg/ml) at 37° C. for 10 minutes and inhibiting a residual trypsin activity with soybean trypsin inhibitor (50 μg/ml). The origins and substrates of other enzymes are shown in Table 1. A concentration of each enzyme inhibiting 50% of activity ($IC_{50}$ value) is also shown in Table 1.

As seen from Table 1, BE-16627A and B of the present invention specifically inhibited the activity of metal enzymes, and most strongly inhibited stromelysin (human), and next strongly inhibited collagenase and thermolysin.

The cytotoxic test for BE-16627A to mouse cultured cancer cells (P388) showed an $IC_{50}$ value of at least 100 μg/ml.

TABLE 1

| Enzyme-inhibitory activity of BE-16627 A and B | | | | |
|---|---|---|---|---|
| Name of enzyme | Origin of enzyme | Substrate | $IC_{50}$ (μM) BE-16627A | BE-16627B |
| Stromelysin | Human (Recombinant) | A | 5.0 | 0.58 |
| Collagenase | Chlostridium histriticum | A | 11.6 | 2.70 |
| Thermolysin | Bacillus thermoproteolyticus | A | 19.3 | 2.40 |
| Trypsin | Bovine | A | >276 | >266 |
| Chymotrypsin | Bovine | A | >276 | >266 |
| Elastase | Porcine | B | >276 | >266 |
| Papain | Papaya latex | A | 138 | >266 |
| Pepsin | Porcine | A | >276 | >266 |

Note
Substrate A: $^3$H-casein
Substrate B: Succinyl-alanyl-prolyl-alanyl-methylcumarylamide As described above, BE-16627A and B of the present invention show a remarkable inhibitory action to stromelysin (human). Therefore, the present substances are useful as a therapeutic agent for various diseases caused by an increase of stromelysin activity, such as metastasis and infiltration of cancer cells, rheumatoid arthritis, gingival inflammation, glomerulonephritis and the like.

The present compounds, when used as stromelysin inhibitor, are also, used alone in an effective amount, or as a pharmaceutical composition comprising an effective amount of the present compound and a pharmaceutically acceptable carrier.

The present pharmaceutical composition is prepared by combining the present compound and an inactive pharmaceutical carrier, and is administered orally, parenterally or topically in various formulations. Examples of adequate compositions include solid compositions for oral administration such as tablet, capsules, dragées, powder, particles, and liquid compositions for oral administration such as suspensions, emulsions. Further, the pharmaceutical compositions can be prepared in the form of a sterilized composition, which can be reconstructed in sterilized water, physiological saline or other injectable sterilized solvents immediately before use.

Pharmaceutically acceptable salts of the present compounds include alkali-addition salts formed by adding an equivalent mole amount of an alkali such as sodium hydroxide, potassium hydroxide or sodium bicarbonate, or an organic amine such as triethylamine or 2-aminoethanol to the present compound. Note, a preferable administration dose of the present compound varies depending on the kind of compound used, the kind of composition formulated, the frequency of administration and the site to be treated, and the host and the state of a disease. A dose for an adult per day is 10 to 500 mg for an oral administration, and 10 to 100 mg per day for a parenteral administration, and preferably, an intravenous administration. Note, the number of administration is 1 to several times, although this varies in accordance with the manner of administration and the state of the disease.

Next, a process for the production of the present compounds BE-16627A and B-is described.

Any microorganisms and mutants thereof producing the BE-16627 compounds can be used to produce the present BE-16627 compounds; for example, a microorganism having the following taxonomical properties can be used. This microorganism was isolated from a soil sample from Kitadake mountain in Yamanashi-ken, in October 1988.

1. Morphology

This strain forms well extended branched substrate mycelia and hyphae, and whirls and fragmen fation of hypa are not observed. Chains of spores (at least 20) are formed on the hyphae, and the shape of the chain is linear or wavy.

The surface of the spore is smooth, and the shape of the spore is cylindrical and it has a size of $1.6 \times 0.8 \sim 1.0 \times 0.6$ μm, and special organs such as sporangium, flagella spore and sclerotium are not observed.

2. Morphology of culture on various agar plate media

The results obtained by culturing the present strain on various agar plate media, at 28° C. for 4 hours, are shown in Table 2.

TABLE 2

| Medium | Growth | Hyphae | Color of | Soluble pigment |
|---|---|---|---|---|
| Yeast.Malt.Agar (ISP2) | Abundant | Abundant; Powder, Grayish white | Pale yellow | None |
| Oat Meal.Agar (ISP3) | Very Abundant | Abundant Powder, Grayish white | Pale yellow | None |
| Starch.Inorganic Salt.Agar (ISP4) | Very Abundant | Abundant Powder gray | Yellowish brown | None |
| Glycerin. Asparagine Agar (ISP5) | Poor | Not formed | Colorless | None |
| Peptone.Yeast. Iron.Agar (ISP6) | Poor | Not formed | Colorless | None |
| Tyrosine.Agar (ISP7) | Poor | Not formed | Colorless | None |
| Nutrient agar | Poor | Not formed | Colorless | None |
| Sucrose.Nitrate Agar | Poor | Poorly formed Powder, White | Colorless | None |
| Glucose. Asparagine.Agar | Abundant | Abundant; Powder, Yellowish white | Colorless | None |

3. Temperature for growth (yeast malt agar medium, culturing for 14 days)
  5° C.: No growth
  10° C.: Poor growth and hyphae formation
  12° C.: Abundant growth and hyphae formation
  17° C.: Very abundant growth and hyphae formation
  20° C.: Very abundant growth and hyphae formation
  28° C.: Very abundant growth and hyphae formation
  35° C.: No growth
  37° C.: No growth
4. Physiological properties

| | |
|---|---|
| (1) Liquefaction of gelatin (Glucose.peptone.gelatin medium) | Positive |
| (2) Hydrolysis of starch (Starch.inorganic salts agar medium) | Positive |
| (3) Coagulation of skim milk (Skim milk medium) | Negative |
| (4) Peptonation of skim milk | Positive |
| (5) Formation of melanin-like pigment | Negative |
| (6) Resistance to sodium chloride (Yeast.malt agar medium) | Growth up to 2% sodium chloride |

5. Utilization of carbon source the strains was cultured on Pridham-Gottlieb medium as a basal medium, and supplemented with different sugars as described below, at 28° C. for 14 days. The results are shown in Table 3.

TABLE 3

| | |
|---|---|
| Glucose | + |
| D-Xylose | + |
| L-Arabinose | + |
| L-Rhamnose | + |
| D-Fructose | ± |
| D-Galactose | + |
| Raffinose | − |
| D-Mannitol | ± |
| Inositol | ± |
| Salicin | ± |
| Sucrose | ± |

Note:
+ utilized
± unclear
− not utilized

6. Composition of cell wall

LL-Diaminopimelic acid is detected, and from the above-mentioned taxonomical properties, the present strain was found to belong to the genus Streptomyces. Accordingly, the present strain was designated as Streptomyces sp. A16627.

Note, the present strain was deposited with the Fermentation Research Institute, Agency of Industrial Science and Technology, the Ministry of International Trade, Japan, as FERM BP-3126.

Mutants used in the present invention and producing BE-16627 compounds are microorganisms mutated with a conventional mutation method, such as irradiation with X-rays or UV-rays, treatment with a mutagen such as nitrogen mustard, azaserine, nitrous acid, 2-aminopurine or N-methyl-N'-nitro-N-nitrosoguanidine (NTG), contact with phage, transformation, transduction, or conjugation.

For the production of the present BE-16627 compounds, a BE-16627 producer strain is inoculated to a medium containing nutrient sources and aerobically grown to obtain a culture broth containing BE-16627 compounds. As the nutrient sources, substances known as nutrient sources for an actinomyces can be used. For example, as a carbon source, commercially available glucose, glycerol, maltose, starch, sucrose, molasses, dextrin or the like is used alone on in combination. As a nitrogen source, commercially available soybean powder, corn steep liquor, meat extract, yeast extract, cotton seed meal, peptone, malt, fish meal, inorganic ammonium salts or sodium nitrate or the like is used alone or in combination. As an inorganic salt, commercially available calcium carbonate, sodium chloride, potassium chloride, magnesium sulfate, various phosphate salts or the like can be used. If necessary, salts of a heavy metal such as iron, manganese or zinc may be added. Moreover, when foaming is violent, as an antiformer, a plant oil such as soybean oil or linseed oil, a higher alcohol such as octadecanol, silicone antifoamer, or the like may be added. Moreover, any additives utilized by the producer strain, and serving to produce BE-16627 compounds may be used.

Any culturing method used in the production of microbial metabolites, including a solid culture and a liquid culture, may be used. The liquid culture is preferably carried out as a shaking culture or a submerged culture with aeration and agitation, although a stationary culture, agitating culture, shaking culture, aeration culture or the like may be carried out. The temperature for culturing is adequately 20° C. to 37° C., and preferably 25° C. to 30° C. A pH value of a medium is preferably 4 to 8, and the culturing time is 24 hours to 192 hours, preferably 48 hours to 144 hours.

To recover a desired product, BE-16627 compounds from a cultured product, any usual isolation means can be used to recover a desired product from a microbial culture. Since the present BE-16627 compounds are present in a culture filtrate, they can be purified from a culture filtrate by a usual isolation means, for example, solvent extraction, ion exchange resin method, or absorption- or partition-chromatography, and gel filtration and the like, used alone or in combination. Moreover, a high performance liquid chromatography and thin layer chromatography may be used for the purification.

As an example of preferred isolation-purification processes, the following process can be mentioned. First, a culture filtrate is centrifuged to separate cells and a culture supernatant, the supernatant is acidified and extracted with an organic solvent, and the extract is concentrated under a reduced pressure to obtain a crude product containing BE-16627 compounds. The crude product thus-obtained is subjected to column chromatography using Diaion HP-20 (Mitsubishi Kasei), column chromatography using DEAE-Sephadex A-25 (Pharmacia), and high performance liquid chromatography using a capcell pak-$C_{18}$ (Shiseido), to obtain BE-16627 compounds of the present invention as a white powder.

BEST MODE OF CARRYING OUT THE INVENTION

Figure 1:
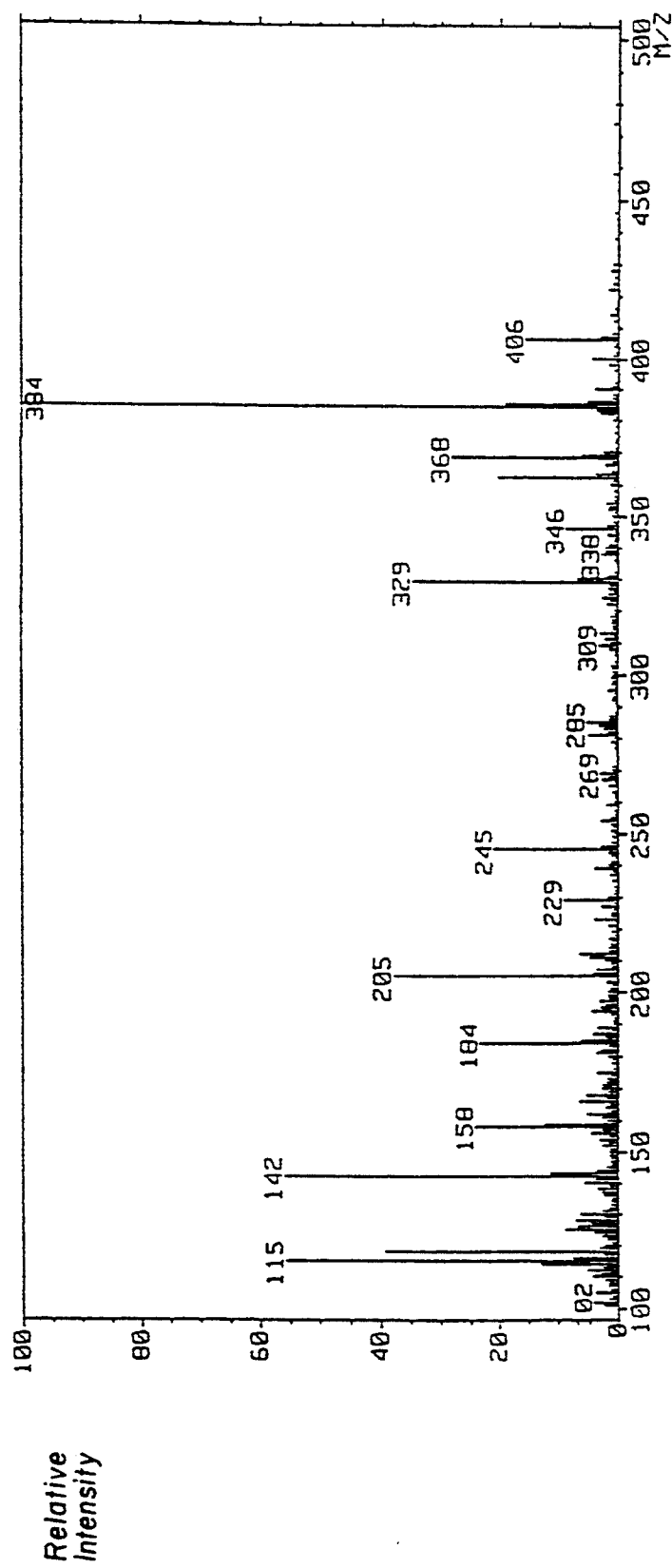
FIGS. 1 and 5 are FAB-Mass spectra of BE-16627A and B, respectively.
Figure 2:
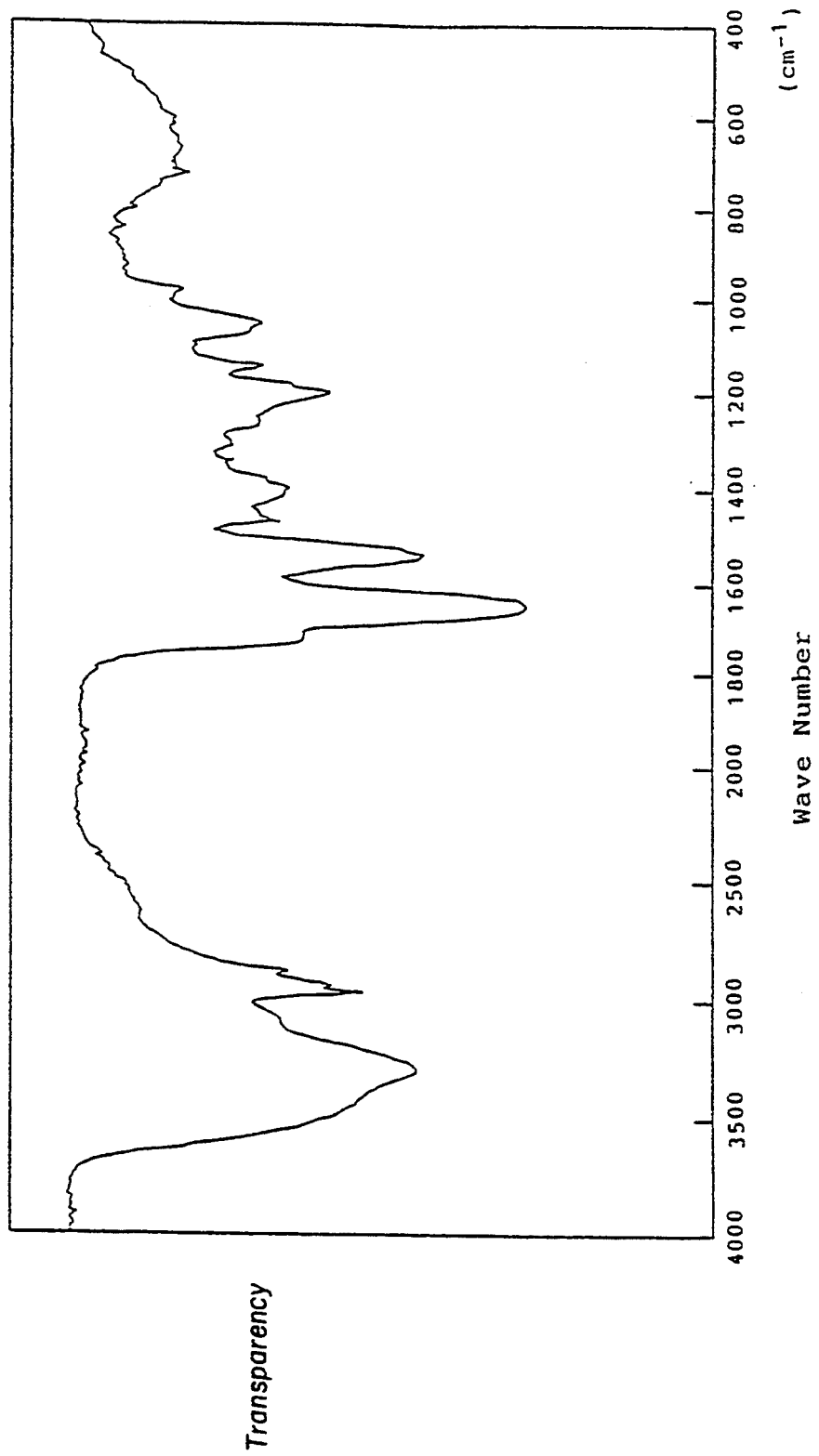
FIGS. 2 and 6 are UV absorption spectra obtained by KBr tablet method for BE-16627A and B, respectively.
Figure 3:
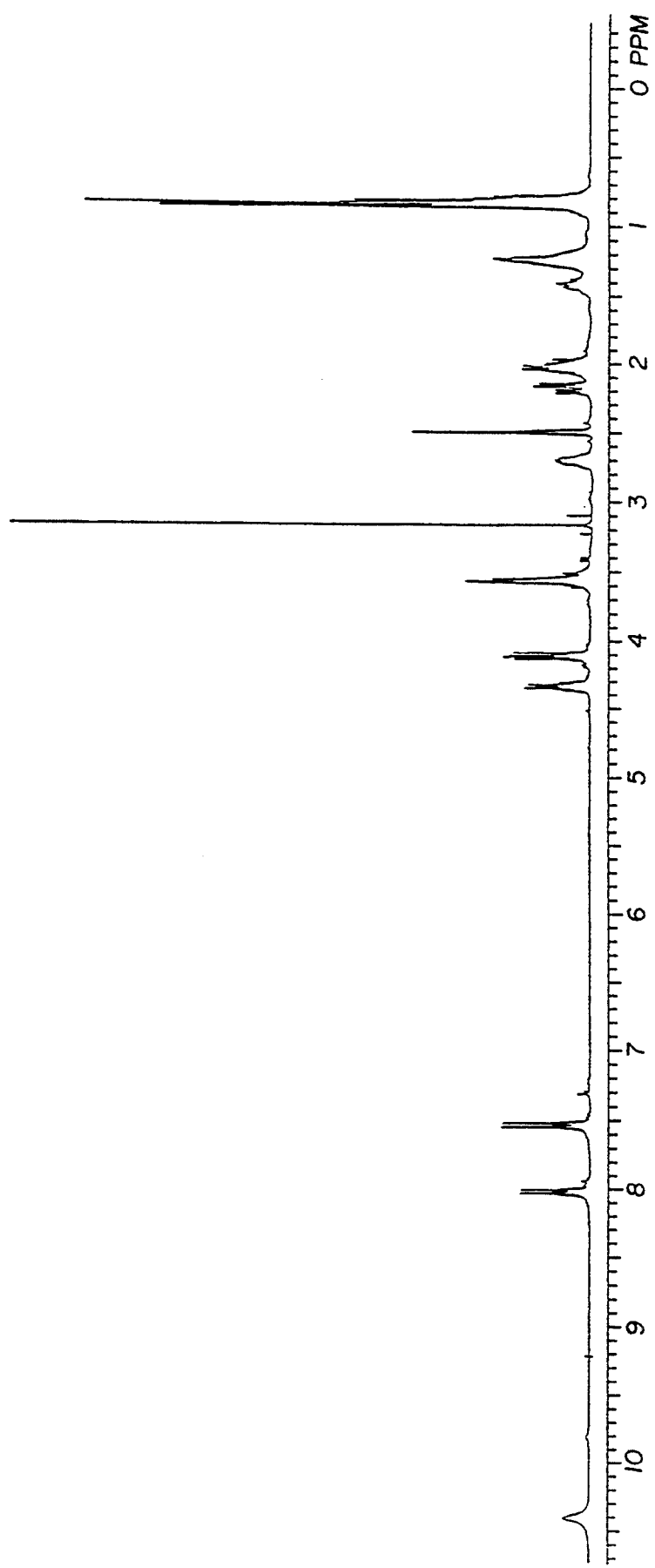
FIGS. 3 and 7 are $^1$H-NMR (300 MHz) spectra measured in $d_6$-dimethylsulfoxide for BE-16627A and B, respectively.
Figure 4:
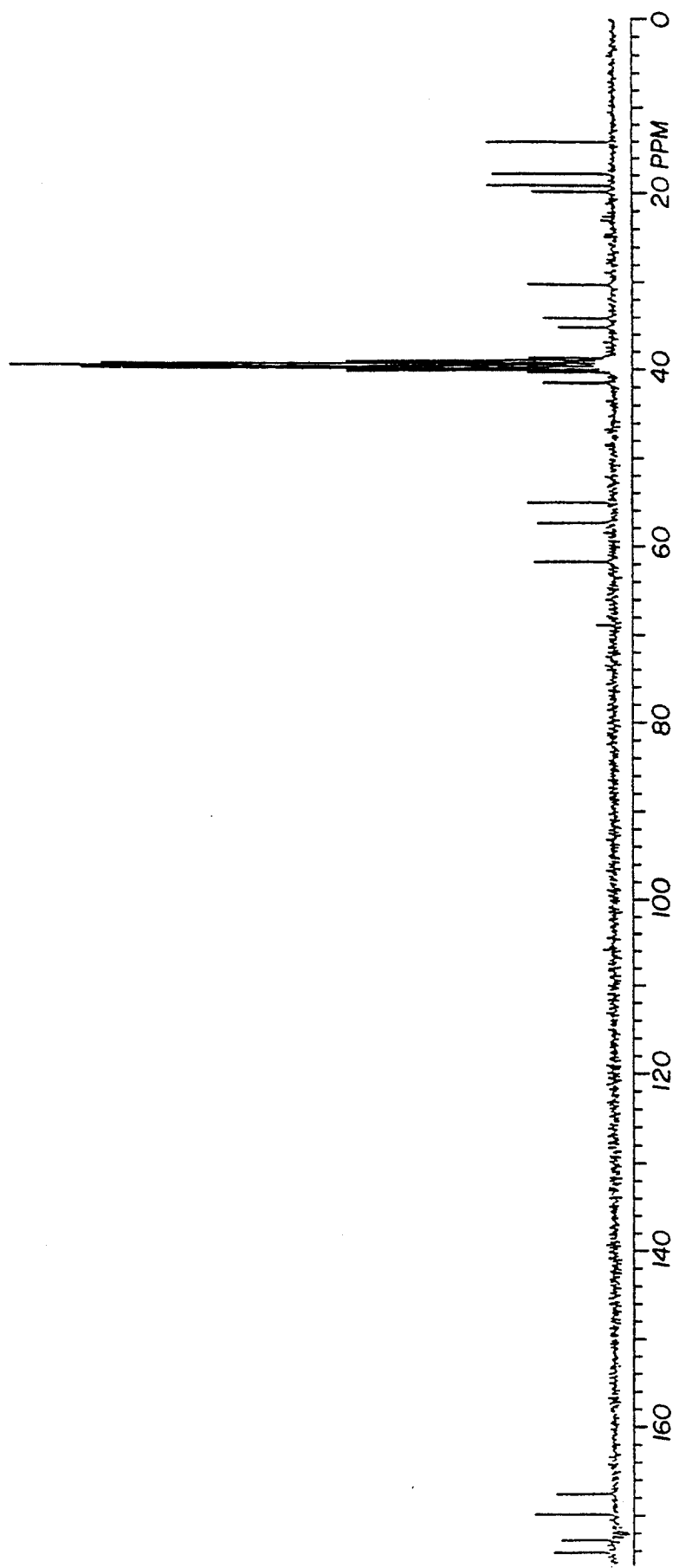
FIGS. 4 and 8 are $^{13}$C-NMR (75 MHz) spectra measured in $d_6$-dimethylsulfoxide for BE-16627A and B, respectively.
Figure 5:
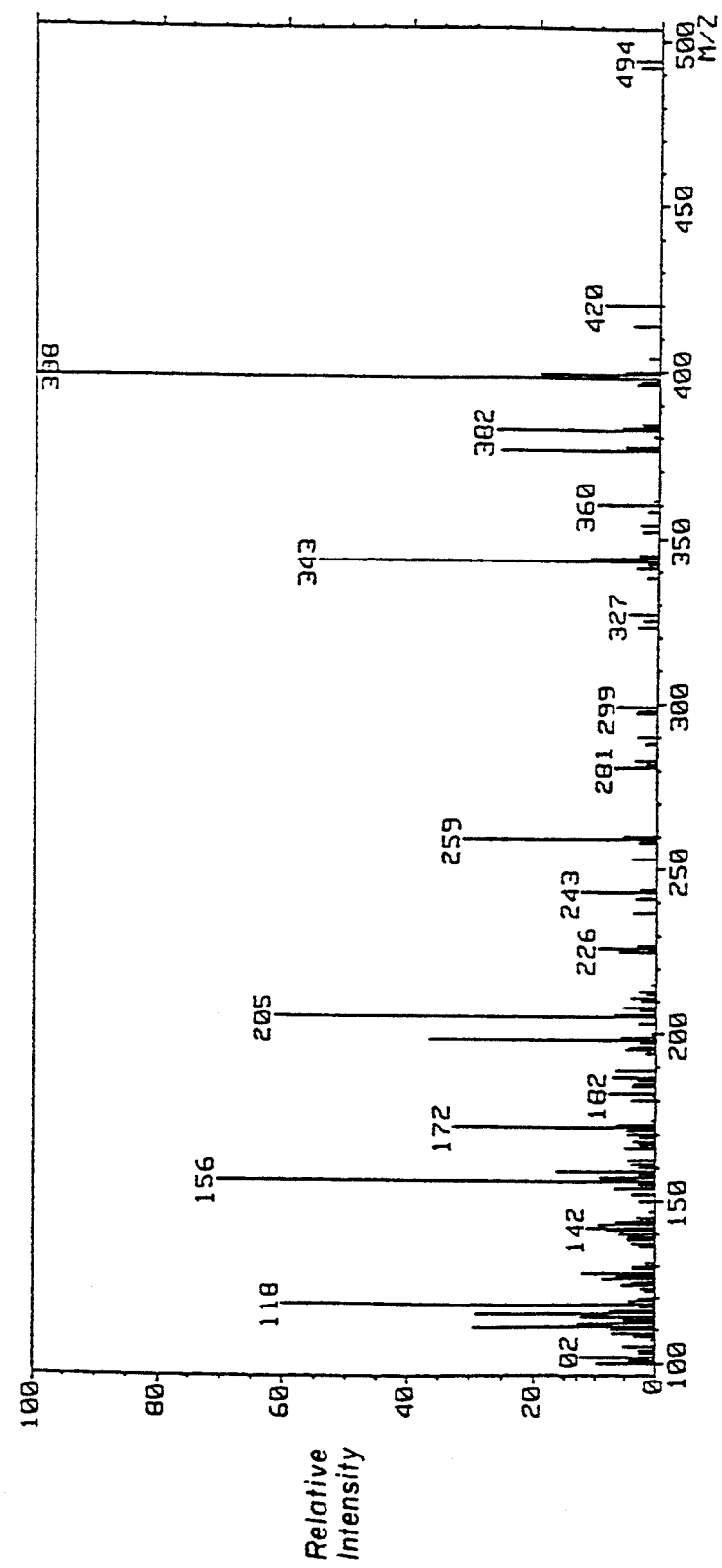
Figure 6:
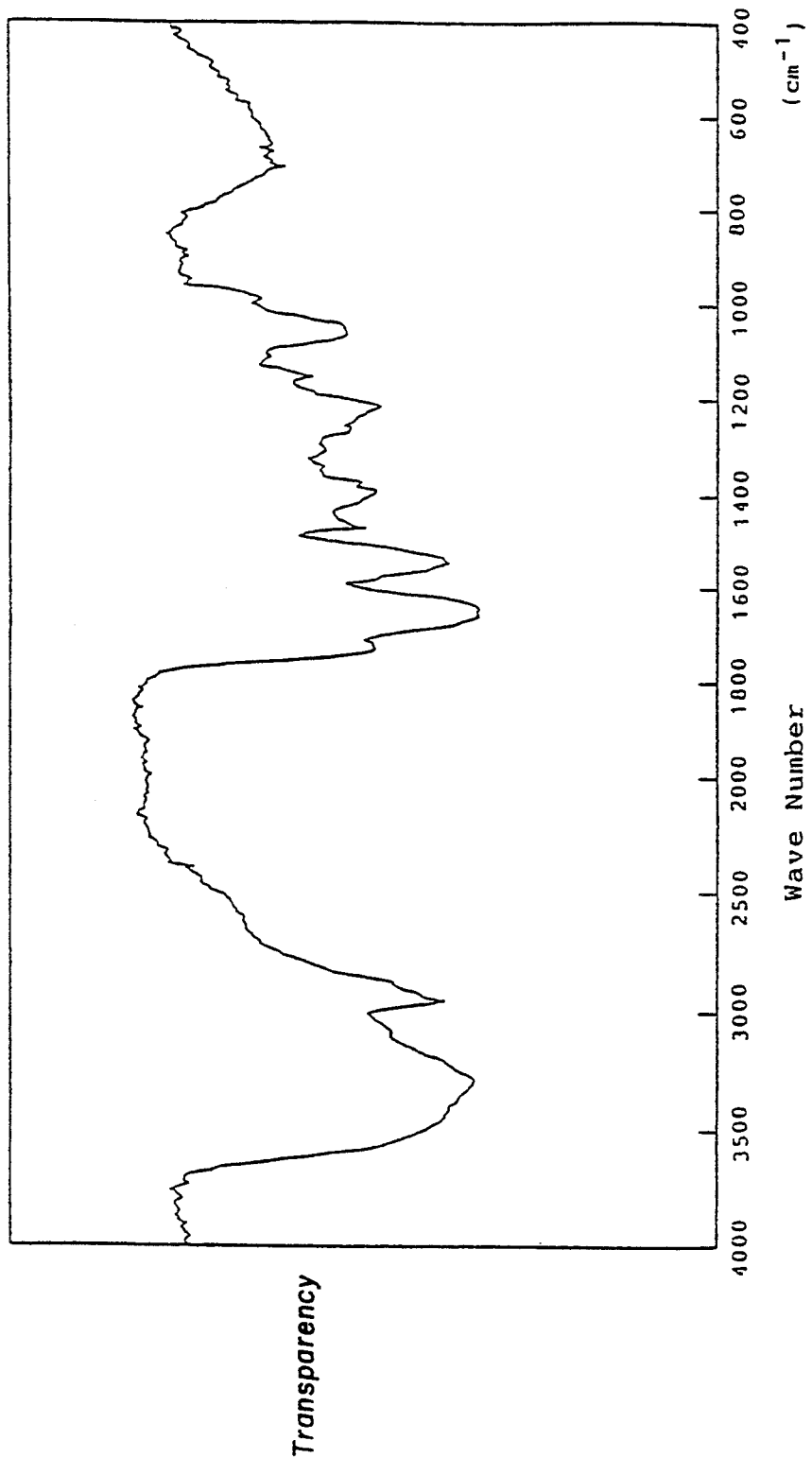
Figure 7:
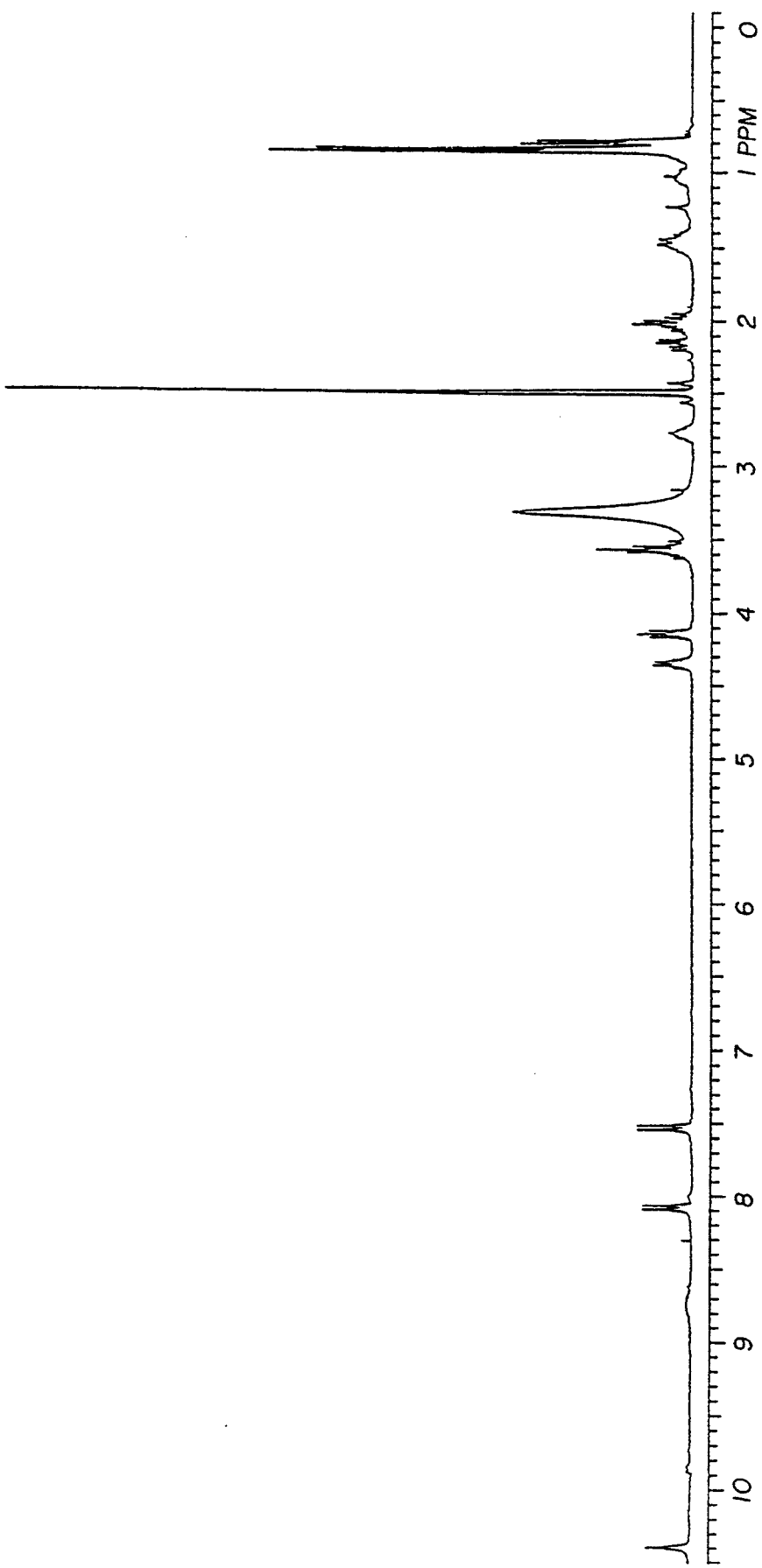
Figure 8:
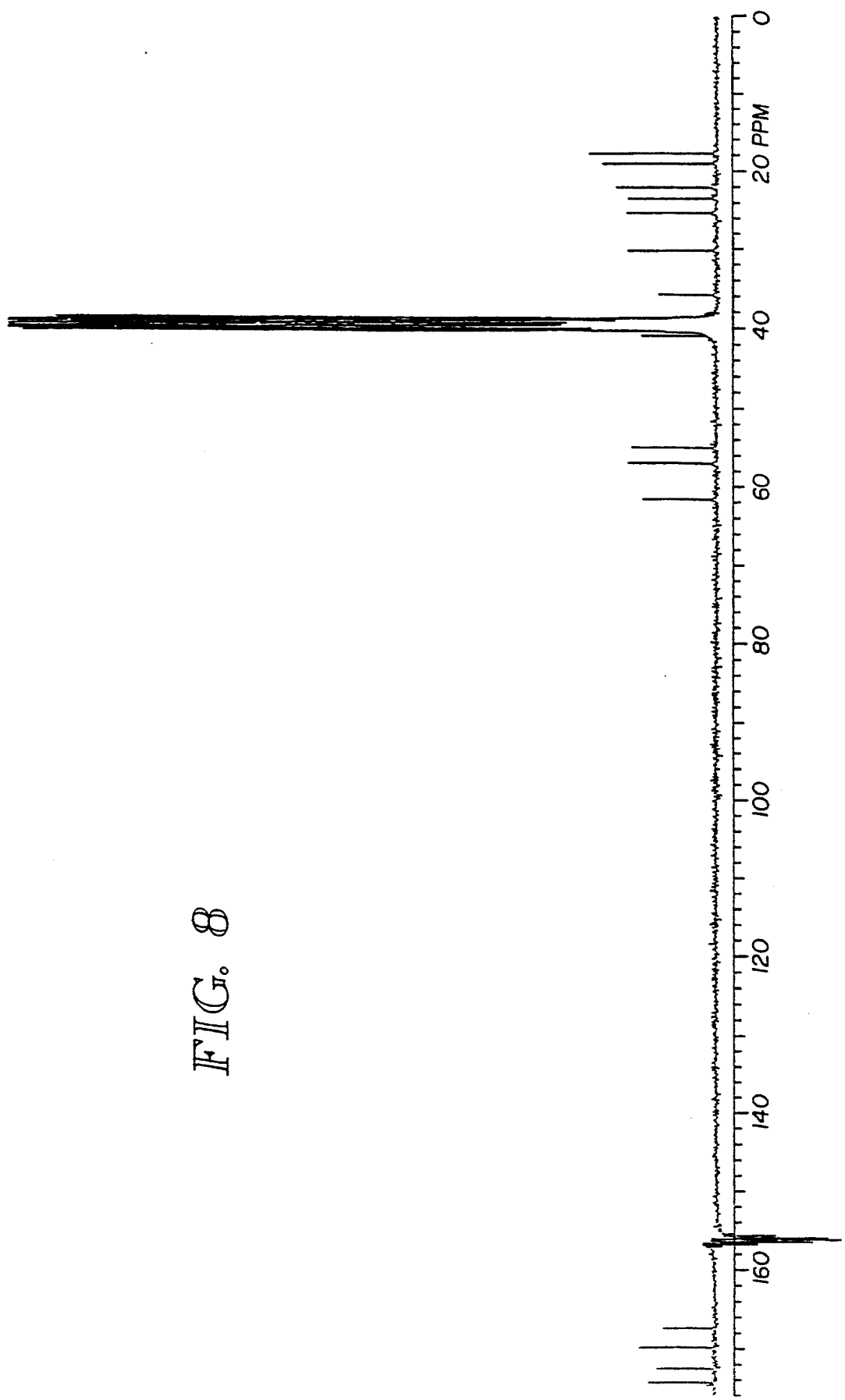

Next, the present invention is more specifically explained by way of Examples, but the present invention is not limited to these Examples, and includes not only modifications of the Examples but also any processes using conventional means for the production, concentration, extraction and purification of the BE-16627 compounds, on the basis of properties of the BE-16627 compound shown by the present invention.

Example

An actinomyces A16627 strain cultured on a slant agar medium was inoculated in 4 conical flasks having 500 ml volume containing 100 ml of a medium (pH 6.7) containing, by weight, 0.1% glucose, 2.0% dextrin, 1.0% corn gluten meal, 0.5% fish meal, 0.1% yeast extract, 0.1% sodium chloride, 0.05% magnesium sulfate, 0.05% calcium chloride, 0.0002% ferrous sulfate, 0.00004% cupric chloride, 0.00004% manganese chloride, 0.00004% cobalt chloride, 0.00008% zinc sulfate, 0.00008% sodium borate, 0.00024% ammonium molybdate and 0.5% 3-(N-morpholino) propane sulfonic acid, and cultured at 28° C. for 72 hours on a rotary shaker (180 rotations per minute). Then, 2 ml of this culture was inoculated to each of 100 500 ml volume conical flasks containing 100 ml of the above-mentioned medium, and culturing was carried out at 28° C. for 124 hours on a rotary shaker (180 rotations per minute). The cultured broth (10 liters) was filtered to obtain 8.5 liters of a culture filtrate, which was then adjusted to a pH of 2.0 with 2N hydrochloric acid, and extracted with 8.5 l of n-butanol. The n-butanol layer was recovered, 4 liters of deionized water was added thereon, and the aqueous layer was adjusted to a pH of 9.0, to transfer the active substances to the aqueous layer. The aqueous layer was separated, and after removing n-butanol contained in the aqueous layer under a reduced pressure, adjusted to a pH of 3.0 with 2N hydrochloric acid. This aqueous solution was applied to a column (4 cm×40 cm) of Diaion HP-20, and after washing the column with 1 liter deionized water, the active substances were eluted with 1 l of 50% aqueous methanol. The elute was concentrated under a reduced pressure to obtain 1.1 g of a crude product, 1.1 g of the crude product thus-obtained was dissolved in 400 ml of 0.01M sodium formate, and the solution was applied to a column (2 cm×30 cm) of DEAE-Sephadex A-25. The active substances were eluted using a linear concentration gradient of 1 liter of 0.01M sodium formate and 1 liter of 0.3M sodium formate, and the elute was fractionated into 15 g fractions. In this case, the active substances were eluted in fractions Nos. 48 to 60. To eliminate sodium formate contained in the active fractions, the active fractions were combined, and after adjusting to a pH of 3.0 with 2N hydrochloric acid, applied to a column (2 cm×20 cm) of Diaion HP-20, which was then washed with water, and the active substances were eluted using 200 ml of 80% methanol to obtain 0.25 g of crude substances. Then, 0.25 g of the crude substances was subjected to high performance liquid chromatography (Capcell pak $C_{18}$, 20 cm×150 cm, Shiseido), and an elution was carried out at a flow rate of 10 ml/min., using a elution medium of acetonitrile/0.1% trifluoroacetic acid by volume (15:85). BE-16627A was obtained at a retention time of from 27 minutes to 29 minutes, and BE-16627B at a retention time of from 57 minutes to 60 minutes. The active fractions of BE-16627A and BE-16627B were separately concentrated and dried under a reduced pressure, and each residue dissolved in methanol. Each methanol solutions was then applied to a column (1 cm×30 cm) of Sephadex LH-20, eluted with methanol, and each active fraction was concentrated under a reduced pressure to obtain 9.7 mg of BE-16627A and 7.1 mg of BE-16627B, respectively, as white powders.

Field of Utilization in Industry

Since the present compounds BE-16627A and B have a low cytotoxicity and strongly inhibit a metallo enzyme, stromelysin (human), they are useful for the treatment and prophylaxis of diseases such as metastasis and infiltration of cancer cells, rheumatoid arthritis, gingival inflammation, glomerulonephritis and the like caused by a degradation of an outer cellular matrix involving the enzyme.

We claim:

1. A process for production of a physiologically active substance BE-16627 represented by the general formula:

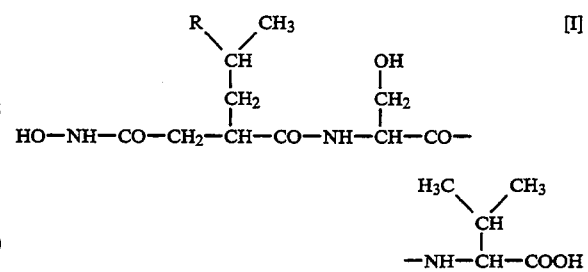

wherein R represents a hydrogen atom or a methyl group, or a pharmaceutically acceptable salt thereof, characterized by culturing Streptomyces sp. A16627 or a mutant thereof producing the substance BE-16627 to accumulate the substance BE-16627, and recovering the same.

2. Biologically pure Streptomyces sp. A16627 or a mutant thereof having an ability to produce a physiologically active substance BE-16627.

* * * * *